United States Patent [19]
Rizkalla

[11] Patent Number: 5,374,748
[45] Date of Patent: Dec. 20, 1994

[54] PROCESS FOR PREPARING SILVER CATALYST FOR ETHYLENE EPOXIDATION

[75] Inventor: Nabil Rizkalla, River Vale, N.J.

[73] Assignee: Scientific Design Company, Inc., Little Ferry, N.J.

[21] Appl. No.: 222,016

[22] Filed: Apr. 4, 1994

Related U.S. Application Data

[62] Division of Ser. No. 24,477, Mar. 1, 1993.

[51] Int. Cl.$^5$ .............. C07D 301/10; C07D 303/04; B01J 23/48
[52] U.S. Cl. .................. 549/534; 502/347; 502/348
[58] Field of Search .......................... 549/534

[56] References Cited

U.S. PATENT DOCUMENTS

| | | | |
|---|---|---|---|
| 4,033,903 | 7/1977 | Maxwell | 502/347 |
| 4,066,575 | 1/1978 | Winnick | 502/347 X |
| 4,342,667 | 8/1982 | Armstrong et al. | 502/347 |
| 4,350,616 | 9/1982 | Boussert | 502/348 |
| 4,374,260 | 2/1983 | Cavitt | 502/347 X |
| 4,389,338 | 6/1983 | Mitsuhata et al. | 502/347 X |
| 4,555,501 | 10/1985 | Armstrong | 502/347 X |
| 4,663,303 | 5/1987 | Becker et al. | 502/347 X |
| 4,760,042 | 7/1988 | Armstrong | 502/348 |
| 4,897,376 | 1/1990 | Liu | 502/347 |
| 5,008,413 | 4/1991 | Liu | 549/534 |

FOREIGN PATENT DOCUMENTS

| | | | |
|---|---|---|---|
| 0241391 | 10/1987 | European Pat. Off. | 502/347 |
| 5015427 | 2/1980 | Japan | 502/347 |
| 6108533 | 8/1981 | Japan | 502/348 |
| 2043481 | 10/1980 | United Kingdom . | |
| 2045636 | 11/1980 | United Kingdom . | |

*Primary Examiner*—Joseph E. Evans
*Attorney, Agent, or Firm*—Kenneth H. Johnson

[57] ABSTRACT

An improved silver catalyst for the oxidation of ethylene with molecular oxygen is made by impregnating a porous support with a silver salt of an acid; subjecting the impregnated support to a multi-stage activation in an atmosphere containing less oxygen than air by heating at a first temperature in the range of 150° to 200° C. for less than an hour, heating at a second temperature in the range of from greater than 200° C. to 300° C. for less than one hour, heating at a third temperature in the range of from greater than 300° C. to 400° C. for less than one hour and finally heating at a fourth temperature in the range of from greater than 400° C. to 500° C.; and post impregnating the support with an alkali metal, preferably cesium, from an anhydrous alcohol solution followed by washing with alcohol solvent and rapid drying to produce a finished catalyst having from $1$–$6 \times 10^{-3}$ gew of the alkali metal per kg of catalyst.

15 Claims, No Drawings

PROCESS FOR PREPARING SILVER CATALYST FOR ETHYLENE EPOXIDATION

This is a division of application Ser. No. 08/024,477, filed Mar. 3, 1993.

BACKGROUND OF THE INVENTION

1. Field of the Invention

The present invention relates generally to a supported silver catalyst useful for the vapor-phase oxidation of ethylene to ethylene oxide. More particularly, the present invention relates to a method of preparing an improved supported silver catalyst post impregnated with cesium.

2. Related Art

The use of supported silver catalysts for the oxidation of ethylene to ethylene oxide has been long known in the art. Additionally, over the years various promoting metals have been added to further enhance performance. In particular, the use of alkali metals has been disclosed in various amounts and added by different methods. A very extensive review of the patent literature is given in G.B. No. 2,043,481A. Such disclosures have been somewhat inconsistent in their teachings, as can be seen by comparing U.S. Pat. No. 2,238,474 in which sodium and lithium hydroxides were suggested as promoters and potassium and cesium were shown to be poisons to U.S. Pat. No. 2,671,764 where rubidium and cesium sulfates were suggested as promoting compounds.

Although alkali metals were suggested generally in the earlier disclosures, it is also generally true that more recent workers in the field have considered potassium, rubidium, and cesium as the preferred alkali metals. For example, see the series of patents to Nielson, et al., in which these materials were used in small amounts co-deposited with the silver—U.S. Pat. Nos. 3,962,136; 4,010,115, and 4,012,425. Still more recently the art has emphasized synergistic combinations of the alkali metals. For example, see G.B. No. 2,043,481A cited above and U.S. Pat. Nos. 4,212,772 or 4,226,782. The art teaches, in addition, that the alkali metals may be used to rejuvenate used catalysts, as for example U.S. Pat. Nos. 4,123,385; 4,033,903; 4,177,169; and 4,186,106. The art teaches that the alkali metals may be deposited either before the silver is placed on the support (pre-deposited)—U.S. Pat. No. 4,207,210; at the same time the silver is deposited (co-deposited)—U.S. Pat. Nos. 4,066,575 and 4,248,741; or subsequent to deposition of the silver (post-deposited)—G.B. No. 2,045,636A.

The amount of alkali metal was suggested to be in quite a wide range in the older art. It was often indicated that large quantities, e.g. up to several per cent of an alkali metal could be used. More recently, the art generally has taught that small quantities of alkali metals produce the optimum effect no matter when the silver and the alkali metals were deposited. Kilty in U.S. Pat. No. 4,207,210 related the optimum amount of alkali metal to the surface area of the support. Exceptions to the above include patents issued to ICI which teach the use of large amounts of sodium alone (G.B. No. 1,560,480) and potassium in combination with smaller amounts of rubidium and cesium (U.S. Pat. No. 4,226,782). However, the art generally teaches that the optimum will be found in substantially lower quantities, perhaps on the order of 50–500 ppm by weight.

It has long been recognized that the method of preparing the catalyst affects its performance. The differing heat "reactivations'" bear witness to this. Additionally, the impregnating solutions used and the intermediate steps have been found to effect the final catalyst. For example, Winnick in commonly assigned U.S. Pat. No. 4,066,575 discloses an impregnating solution containing silver lactate, lactic acid, barium acetate, hydrogen peroxide and water. As a class the lactate based catalyst are very stable but exhibit low selectivity. The support is impregnated with the solution and then first activated by heating in an inert atmosphere at 350° C. for and then dried in air at 200° C. for 12 hours. The "activated" catalyst is then impregnated with a cesium solution and dried in air at 130° C. for 3 hours. The use of the inert atmosphere during the activation step produced a catalyst that was more selective, but much less stable, i.e., the catalyst lost its activity fairly quickly resulting in shorter run length for a given end of run temperature.

Armstrong, in commonly assigned U.S. Pat. No. 4,555,501 disclosed using an impregnating solution containing the silver salt of a neo acid. The impregnated support was then "activated" at temperatures of about 200° C. to 600° C. in the presence of air or reduced oxygen atmospheres, the presence of some oxygen being desirable. The alkali metal, if desired, was then deposited in small quantities (in the range of 260 wppm).

Cesium now appears to be the preferred alkali metal. Various sources of cesium are catalogued in the prior art, for example, cesium hydroxide, cesium nitrate, cesium chloride, cesium chlorate, cesium bicarbonate, cesium carbonate, and other anion functionalities such as formates, acetates and the like.

U.S. Pat. No. 4,374,260 discloses the coprecipitation of silver and cesium salt, such as the carbonate from a silver carboxylate/amino complex.

U.S. Pat. Nos. 4,3350,616 and 4,389,338 both show the deposition of $CsCO_3$ on to activated silver catalyst from alcohol solution where the silver was derived from aqueous silver salt solution.

U.S. Pat. Nos. 4,066,575 and 4,033,903 disclose the preparation of silver catalyst from both aqueous and non aqueous salt solutions and subsequent treatment of the activated silver catalyst with post deposition of an alkali metal salt such as cesium and anions from lower alcohol and preferable from aqueous solutions. Similarly U.S. Pat. No. 4,342,667 discloses the post deposition of cesium on to silver catalyst derived from aqueous solutions.

What is most clear is from the prior art relating to post deposition alkali metal is the general interchangeability of aqueous and non aqueous procedures, i.e. silver catalyst may be prepared by either aqueous or non aqueous procedures and the post deposition of alkali metal may be aqueous or non aqueous. Furthermore, the salt of silver or alkali metal is not specific. Generally the procedures tended to favor the presence of water.

It has now been found that water at any stage and in any amount is detrimental to the performance of the final catalyst. Thus, the present preparation is characterized as being substantially anhydrous with post disposition of alkali metal, e.g. cesium.

It is an advantage of the present invention that catalysts of exceptional stability in use for the preparation of ethylene oxide are produced, which have high selectivity at high conversions for the ethylene oxide process.

SUMMARY OF THE INVENTION

Briefly stated one aspect of the present invention is a catalyst prepared by the process of impregnating a porous support having a low surface area with a hydrocarbon solution of a silver salt of an organic acid which is substantially free of water and acid and activated by heating in multi-stages in an atmosphere containing less oxygen than air in order to control the combustion of the organic portion of the acid silver salt. A preferred series of stages is a first temperature in the range of 150° to 200° C. for less than an hour, preferably said first activation is carried out in an atmosphere containing less than 20 vol % oxygen, heating at a second temperature in the range of from greater than 200° C. to 300° C. for less than one hour, heating at a third temperature in the range of 300° C. to 400° C. and finally heating at a fourth temperature in the range of from greater than 400° C. to 500 ° C. for less than one hour. Preferably each of the heating steps is from 1 to 30 minutes in duration. The heating atmosphere is controlled to eliminate uncontrolled combustion of the organic portions of the silver salt or solvents by controlling and adjusting the amount of oxygen present during said heating. Preferably the atmosphere contains less than 3 vol % oxygen of the total atmosphere. The activation produces a support containing the activated silver.

The catalyst is made by impregnating a porous support, preferably having a surface area in the range of 0.2 to 2.0 $m^2/g$, with a hydrocarbon solution of a silver salt of an organic acid. The solution should be substantially free of both water and acid as this aspect has been shown to be especially beneficial to catalyst performance and hence preferred. The impregnated support is activated by heating wherein, the improvement is the control of the combustion of the organic materials.

In order to modify the activated silver catalyst an alkali metal, preferably cesium, is added.

Another aspect of the invention the activated silver catalyst is a substantially anhydrous post impregnation with an alkali metal, preferably cesium, to produce a finished catalyst by immersing the support in a stationary or circulating stream of the alkali metal in a anhydrous solvent such as ethanol. The optimum amount of alkali metal(s) added will be selected to optimize catalyst performance and will be dependent upon the surface area of the support chosen. That is, more alkali metal will be used on supports which have larger surface area than on those having relatively small surface area. The term anhydrous as used herein means as free of water as possible, but in any event less than 1% water, i.e., substantially anhydrous.

A third aspect of the present invention is the washing of cesium modified silver catalyst with a lower alcohol. Preferably methanol, ethanol, isopropanol or the like are contacted with and impregnated into the catalyst, removed from the catalyst and the catalyst dried.

It is believed that the ionic cesium contacting the alumina of the support, not covered by silver, is more firmly attached to the polar alumina surface than that on the surface of the silver metal. The wash as described preferentially leaches or removes some of the less firmly held cesium on the silver while leaving the desirable modifying cesium on the alumina sites.

The stability achieved by the multi-stage heat activation of silver catalyst is retained and the selectivity is enhanced by both the anhydrous preparation and the final solvent wash.

The catalyst of the present invention may be employed under oxidizing conditions typical to the art for preparing ethylene oxide by the vapor phase oxidation of ethylene with improved results, especially catalyst stability.

The term "inert" as used herein means any gaseous material under the conditions of activation which does not react with silver or any other component of the silver impregnated support. Preferred inert materials include nitrogen, helium and carbon dioxide, but other specific materials including neon, argon, and the like may be used. The limitation of oxygen during the activation is of principal concern.

DETAILED DESCRIPTION AND PREFERRED EMBODIMENT

The catalyst of the present invention may contain from 3 to 25 wt % silver on the support. Preferred catalysts prepared in accordance with this invention contain 3 up to about 20% by weight of silver, expressed as metal, deposited upon the surface and throughout the pores of a porous refractory support. Silver contents higher than 20% by weight of total catalyst are effective, but result in catalysts which are unnecessarily expensive. Silver contents, expressed as metal, of about 5–13% based on weight of total catalyst are preferred, while silver contents of 8–11% are especially preferred.

Catalysts may be made with supports comprising alumina, silica, silica-alumina or combinations thereof. Preferred supports are those containing principally alpha-alumina, particularly those containing up to about 15 wt % silica. Especially preferred supports have a porosity of about 0.1–1.0 cc/g and preferably about 0.2–0.5 cc/g. Preferred supports also have a relatively low surface area, i.e. about 0.2–2.0 $m^2/g$, preferably 0.4–1.6 $m^2/g$ and most preferably 0.5–1.3 $m^2/g$ as determined by the BET method. See J. A. Chem. Soc. 60, 309-16 (1938). Porosities are determined by the mercury porosimeter method; see Drake and Ritter, $\mp$Ind. Eng. Chem. Anal. Ed.," 17, 787 (1945). Pore and pore diameter distributions are determined from the surface area and apparent porosity measurements.

For use in commercial ethylene oxide production applications, the supports are desirably formed into regularly shaped pellets, spheres, rings, etc. Desirably, the support particles used should have "equivalent diameters" in the range from 3–10 mm and preferably in the range of 4–8 mm, which are usually compatible with the internal diameter of the tubes in which the catalyst is placed. "Equivalent diameter" is the diameter of a sphere having the same external surface (i.e. neglecting surface within the pores of the particle) to volume ratio as the support particles being employed.

The silver is added to the support by immersion of the support into a solution containing a silver salt of an organic acid which is substantially free of water and said acid, such as the neo acids (particularly those having at least seven carbon atoms) described in U.S. Pat. No. 4,864,042 which is incorporated herein in its entirety. The silver containing liquid penetrates by absorption, capillary action and/or vacuum into the pores of the support. A single immersion or a series of immersions, with or without intermediate drying, may be used, depending in part upon the concentration of the silver salt in the solution. To obtain catalysts having silver contents within the preferred range, suitable impregnating solutions will generally contain from 5–50 wt % silver, expressed as metal, but supplied as silver salts of organic acids. The exact concentrations employed, of course, will depend upon, among other factors, the desired silver content, the nature of the support, the viscosity of the liquid, and solubility of the acid silver salt.

Impregnation of the selected support is achieved in a conventional manner. The support material is placed in the silver solution until all of the solution is absorbed by the support. Preferably the quantity of the silver solution used to impregnate the porous support is no more than is necessary to fill the pore volume of the porous support.

The impregnating solution, as already indicated, is characterized as a substantially water free and acid free organic solution of a silver salt of an organic acid. A hydrocarbon solvent is employed, such as toluene, cyclohexane, xylene, ethyl benzene, cumene or nonene which would normally be water free. Since water is considered to be detrimental to the preparation of silver catalysts when the method of the invention is used, it should be present in no more than about 0.1 vol % in the silver impregnating solution, preferably less than about 0.01 vol %.

After the multi-stage activation the support may be impregnated with the alkali metal if desired. It is the purpose of alkali metal to modify the catalyst and raise selectivity while leaving the improved stability intact. When used the amount of the alkali metal on the finished catalyst is generally similar to those employed heretofore. Thus the amount deposited will be generally up to about $8 \times 10^{-3}$ gew/kg catalyst, preferably up to about $7 \times 10^{-3}$ gew/kg, and particularly about 1 to $6 \times 10^{-3}$ gew/kg (gew=gram equivalent weight). The alkali metals of the periodic table include sodium, lithium, potassium, rubidium and cesium. For purposes of the present invention, the latter three alkali metals are particularly preferred, especially cesium, although sodium and lithium are not necessarily excluded. The alkali metal salts are dissolved in alcohol solutions, preferably substantially free of water.

In the absence of water in the alcohol solvent, the cesium compound, although poorly soluble, remains evenly distributed through the solvent during evaporization and drying, hence is more evenly distributed over the silver catalyst. Preferably the alkali metal impregnated catalysts are dried rapidly, e.g. one to two minutes at high temperature, e.g. at least 100° C. up to 800° C., preferably around 200° C. to 600 ° C. This may be readily achieved by using a moving belt as described herein or by placing it in a tube and allowing a fast current of hot air to remove the solvent. The drying may be conducted in air or an inert gas.

Catalysts prepared by the procedures above have improved performance, especially stability, for use in the production of ethylene oxide by the vapor phase oxidation of ethylene with molecular oxygen. These usually involve reaction temperatures of about 150° C. to 400° C., usually about 200° C. to 300° C., and reaction pressures in the range of from 0.5 to 35 bar. Reactant feed mixtures contain 0.5 to 20% ethylene and 3 to 15% oxygen, with the balance comprising comparatively inert materials including such substances as nitrogen, carbon dioxide, methane, ethane, argon and the like. Only a portion of the ethylene usually is reacted per pass over the catalyst and after separation of the desired ethylene oxide product and the removal of appropriate purge streams and carbon dioxide to prevent uncontrolled build up of inerts and/or by-products, unreacted materials are returned to the oxidation reactor.

In the following examples the catalysts were made from a cumene solution of a silver salt of neo-decanoic acid as described above. The characteristics of suitable supports are set out below.

The finished catalysts are then tested for activity and selectivity by crushing and placing 36 grams in a micro reactor consisting of a ¼ inch stainless steel tube which is heated in a salt bath. A feed mixture of 7% oxygen, 8% $CO_2$, 15% $C_2H_4$, 70% $N_2$ is passed over the catalyst with a gas space velocity of 5500 $hr^{-1}$. The pressure is maintained at 300 psig (21.69 bar) and the temperature between 200° C. and 300° C. as required to maintain an outlet concentration of 1.5 vol % (160 Kg per hour per $m^3$ of catalyst) ethylene oxide. The activity of the catalyst is expressed as the temperature necessary to maintain the outlet concentration at 1.50 vol % ethylene oxide, the lower the temperature, the more active the catalyst. The selectivity of the catalyst is expressed as the mole % of the total ethylene converted to ethylene oxide at the outlet concentration of 1.50 vol % ethylene. The stability of the catalyst is measured by the increase in temperature required to maintain the ethylene oxide at 1.50 vol % divided by 100 hours and is expressed as °C./100 hr.

EXAMPLE 1 (Comparative)

In this example a conventional activation with aqueous Cs deposition was carried out.

The support used for this preparation was obtained from Norton Company and was made primarily of α-alumina in the form of 5/16 inch cylinders. The support has a surface area of 0.55 $m^2$/g pore volume of 0.3 cc/g, and medium pore diameter of 15μ. A 95 parts of a cumene solution of silver neodecanoate, containing 26 wt % silver, was added to 225 parts of the hot support and the mixture was mixed for 20 minutes. The catalyst was prepared using one step activation with air at 500° C. and was impregnated with cesium hydroxide solution in water/alcohol solvent, which was subsequently dried with vacuum. The catalyst was tested under the condition as outlined above. After 150 hours of reaction time the selectivity to ethylene oxide was 80.9% and the reaction temperature was 232° C. The catalyst's performance did not improve with longer reaction time.

EXAMPLE 2

In this example multi-stage activation was carried out with anhydrous Cs deposition.

The support used for this preparation was obtained from Norton Company and was made primarily of α-alumina in the form of 5/16 inch cylinders. The support has a surface area of 0.55 $m^2$/g, pore volume of 0.3 cc/g, and medium pore diameter of 1.5μ. A 95 parts of a cumene solution of silver neodecanoate, containing 26% silver was added to 225 parts of the hot support and the mixture was mixed for 20 minutes. The deposition of silver compound was induced by heating the catalyst to a temperature that did not exceed 200° C. in a stream of nitrogen. The residence time of the catalyst in the heated zone was 2 minutes on a moving belt. This step was repeated at 300° C. and 400° C.

The catalyst was then impregnated for two hours at room temperature in an anhydrous ethanolic solution that contained 525 ppm cesium bicarbonate. The catalyst was superficially dried by a stream of nitrogen followed by heating on a moving belt at 200° C. The results of the catalyst test are summarized in TABLE 1.

TABLE 1

Results of Catalyst Test

| Life, hr | Temp. °C. | Selectivity %, to EO |
|---|---|---|
| 145 | 237 | 82.8 |
| 500 | 237 | 82.8 |
| 575 | 237 | 83.0 |
| 715 | 236 | 83.0 |

EXAMPLE 3

The support used for this preparation was obtained from Norton Company and was made primarily of α-alumina in the form of 5/16 inch cylinders. The support has a surface area of 0.55 m$^2$/g, pore volume of 0.3 cc/g, and medium pore diameter of 1.5μ. A batch of 225 parts of the support was heated to 80° C. and placed under vacuum, 50 mm Hg, then 95 parts of a cumene solution of silver neodecanoate, containing 26% silver, was added and the mixture was mixed for 20 minutes. The deposition of silver compound was induced by heating the catalyst to a temperature that did not exceed 200° C. in a stream of nitrogen the residence time of the catalyst in the heated zone was 2 minutes. This step was repeated at 300° C. and at 400° C.

The catalyst was then impregnated for two hours at room temperature in an anhydrous ethanolic solution that contained 525 ppm cesium bicarbonate. The catalyst was dried by heating on a moving belt at 200° C. The results of the catalyst test are summarized in the Table 2.

TABLE 2

Results of Catalyst Test

| Life, hr | Temp. °C. | Selectivity %, to EO |
|---|---|---|
| 100 | 231 | 82.5 |
| 300 | 230 | 82.7 |
| 450 | 230 | 83.0 |

EXAMPLE 4

The support used for this preparation was obtained from Norton Company and was made primarily of α-alumina in the form of 5/16 inch cylinders. The support has a surface area of 0.55 m$^2$/g, pore volume of 0.3 cc/g, and medium pore diameter of 1.5μ. 95 parts of a cumene solution of silver neodecanoate, containing 26% silver, was added to 225 parts of the support and the mixture was mixed for 30 minutes.

The deposition of silver was induced by heating the catalyst up to the decomposition temperature of the silver salt. This was achieved via heating in a furnace that has several heating zones in a controlled atmosphere. The catalyst was loaded on a moving belt that entered the furnace at ambient temperature, which was gradually increased as the catalyst passed from one zone to the next. The temperature was increased, up to 400° C. as the catalyst passed through seven heating zones. After the heating zones the belt passed through a cooling zone that gradually cooled the catalyst to a temperature lower than 100° C. The total residence time in the furnace was 22 minutes. The atmosphere of the furnace was controlled to eliminate uncontrolled combustion of the organic portion of the silver salt and solvent. This was achieved via using nitrogen flow in the different heating zones. The amount of nitrogen was sufficient to inhibit any combustion and to remove any evolved fumes during the calcination process.

The catalyst was then impregnated for two hours at room temperature in an anhydrous ethanolic solution containing 525 ppm of cesium bicarbonate. The solution was drained and an equal volume of ethanol was added. The catalyst was mixed with the fresh ethanol to remove any excess cesium present on its surface. The liquid was drained, and the catalyst was dried by placing it on a belt that travelled through a heated zone of a furnace in a current of 200° C. air. The residence time in the hot zone, the air flow and the furnace temperature were sufficient to dry all the solvent in the shortest time possible. The catalyst was crushed and charged in a tube that was heated by a salt bath. A gas mixture containing 15% ethylene, 7% oxygen, and 78% inert, mainly nitrogen and carbon dioxide, was allowed to flow over the catalyst under 300 p.s.i. The temperature of the reaction was adjusted in order to obtain ethylene oxide productivity of 160 Kg ethylene oxide per hour per m$^3$ of catalyst. The results of the catalyst test are summarized in table 3:

TABLE 3

Results of Catalyst Test

| Life, hr | Temp. °C. | Selectivity, % |
|---|---|---|
| 350 | 227 | 82.8 |

EXAMPLE 5

The support used for this preparation was obtained from Norton Company and was made primarily of α-alumina in the form of 5/16 inch cylinders. The support has a surface area of 0.55 m$^2$/g, pore volume of 0.3 cc/g, and medium pore diameter of 1.5μ. 95 parts of a cumene solution of silver neodecanoate, containing 26% silver, was added to 225 parts of the hot support and the mixture was mixed for 30 minutes. The deposition of silver was induced by heating the catalyst to a temperature that did not exceed 150° C. in a stream of nitrogen. The residence time of the catalyst in the heated zone was two minutes. This process was repeated at 200°, 250°, and 300° C. and at 400° C.

The catalyst was then impregnated for two hours at room temperature in an anhydrous ethanolic solution containing 525 ppm of cesium bicarbonate. The solution was drained and an equal volume of ethanol was added. The catalyst was mixed with the fresh ethanol to remove any excess cesium present on its surface. The liquid was drained, and the catalyst was dried by placing it on a belt that travelled through a heated zone of a furnace in a current of 200° C. air. The residence time in the hot zone, the air flow and the furnace temperature were sufficient to dry all the solvent in the shortest time possible.

After drying the catalyst, it was tested in a tube that is heated by a salt bath. A gas mixture containing 15% ethylene, 7% oxygen, and 78% inert, mainly nitrogen and carbon dioxide, was allowed to flow over the catalyst under 300 p.s.i. The temperature of the reaction was adjusted in order to obtain ethylene oxide productivity of 160 Kg per hour per m$^3$ of catalyst. The result of the catalyst test are summarized in table 4:

TABLE 4

| Life, hr | Temp. °C. | Selectivity, % |
|---|---|---|
| 200 | 230 | 83.7 |
| 900 | 230 | 83.7 |

EXAMPLE 6

The support used for this preparation was obtained from Norton Company and was made primarily of α-alumina in the form of 5/16 inch cylinders The support has a surface area of 0.55 m$^2$/g, pore volume of 0.3 cc/g, and medium pore diameter of 1.5μ. 95 parts of a cumene solution of silver neodecanoate, containing 26% silver, was added to 225 parts of the hot support and the mixture was mixed for 20 minutes. The deposition of silver was induced by heating the catalyst to a temperature that did not exceed 150° C. in a stream of a gas mixture containing 2.5% oxygen in nitrogen. The residence time of the catalyst in the heated zone was two minutes. This process was repeated at 200° C., 250° C., 300° C. and at 400° C.

The catalyst was then impregnated for two hours at room temperature in an anhydrous ethanolic solution containing 525 ppm of cesium bicarbonate. The catalyst was dried and tested in a tube that is heated by a salt bath. A gas mixture containing 15% ethylene, 7% oxygen, and 78% inert, mainly nitrogen and carbon dioxide, was allowed to flow over the catalyst under 300 p.s.i. The temperature of the reaction was adjusted in order to obtain ethylene oxide productivity of 160 Kg per hour per m$^3$ of catalyst. The results of the catalyst test are summarized in table 5:

TABLE 5
Results of Catalyst Test

| Life, hr | Temp. °C. | Selectivity % |
|---|---|---|
| 200 | 225 | 81.64 |

EXAMPLE 7

The support used for this preparation was obtained from Norton Company and was made primarily of α-alumina in the form of 5/16 inch cylinders The support has a surface area of 0.55 m$^2$/g, pore volume of 0.3 cc/g, and medium pore diameter of 1.5μ. 95 parts of a cumene solution of silver neodecanoate, containing 26% silver, was added to 225 parts of the hot support and the mixture was mixed for 20 minutes. The deposition of silver was induced by heating the catalyst in a stream of nitrogen.

The catalyst was divided into several equal batches. Each batch was impregnated for two hours at room temperature in an ethanolic solution that contained a specific concentration of water and 525 ppm cesium bicarbonate. The liquid was drained and followed by heating on a moving belt in a current of 200° C. air.

A sample of the catalyst was tested in a tube that is heated by a salt bath. A gas mixture containing 15% ethylene, 7% oxygen, and 78% of inert, mainly nitrogen and carbon dioxide, was allowed to flow over the catalyst under 300 p.s.i. The temperature of the reaction was adjusted in order to obtain ethylene oxide productivity of 160 Kg per hour per m$^3$ of catalyst. The results of the catalyst test are summarized in table 6:

TABLE 6
Effect of Water in Cesium Solution

| Ex. 7 | H$_2$O % | Performance* at 150 Hr Sel (T°C.) |
|---|---|---|
| A | <0.1 | 83.0 (231) |
| B | 0.3 | 82.7 (230) |
| C | 1 | 82.5 (232) |
| D | 2 | 82.0 (228) |
| E | 4 | 82.1 (225) |

* EO = 1.5.

EXAMPLE 8

The method used to dry the solvent is of importance to the catalyst performance. After impregnation with cesium solution, it is rather important to deposit the cesium salt on the catalyst as fast as possible. It was discovered that drying the solvent in a current of hot gas, example heated air, is one of the efficient ways to achieve the fast deposition of the salt. The temperature of the gas has to be high enough to insure the fast precipitation of the cesium salt. Drying the catalyst at a slow rate, as in vacuum or via a current of a low temperature gas, gives a catalyst with poor cesium dispersion and does not lead to the full benefit of the effect of the promoter. The following examples will illustrate the impact of the drying method:

A large batch of catalysts was prepared by impregnating a commercial alpha-alumina support with a solution of silver neodecanoate in cumene, followed by calcining the catalyst via heating at 500° C. in a stream of nitrogen. The batch was divided into 245 g portions and each portion was impregnated for two hours with 300 g of ethanol solution that contain 525 ppm cesium. The wet catalysts were dried using different methods. Table 7 illustrates the effect of the different cesium salts and the drying method on the catalyst's performance:

TABLE 7
The effect of anhydrous Cesium solution and the drying method on Selectivity

| Example 8 | Temp. °C. 100 hr | Temp. °C. 200 hr | Sel. % 100 hr | Sel. % 200 hr | Notes |
|---|---|---|---|---|---|
| A | 233 | 232 | 81.8 | 82.3 | Anhydrous Cs$_2$CO$_3$, Dried fast on belt |
| B | 236 | 237 | 80.7 | 80.9 | CsOH in H$_2$O/ethanol, dried by vacuum for 17 hrs |
| C | 231 | 230 | 80.8 | 81.0 | CsOH in H$_2$O/ethanol, dried on belt, 500° C. |

EO = 1.5
SV = 5500

Example 8A illustrates the effect of both anhydrous cesium salt and the fast drying method. Example 8B is the standard case in which the cesium solution was not anhydrous and the catalyst was dried via maintaining its temperature below 50° C. under reduced pressure, 100 mm Hg, for 17 hours. Example 8C is similar to 8B except a fast drying method was used.

EXAMPLE 9

The support used for this preparation was obtained from Norton Company and was made primarily of α-alumina in the form of 5/16 inch cylinders. The support has a surface area of 0.55 m$^2$/g, pore volume of 0.3 cc/g, and medium pore diameter of 1.5μ. 95 parts of a cumene solution of silver neodecanoate, containing 26% silver, was added to 225 parts of the hot support and the mixture was mixed for 30 minutes. The deposition of silver was induced by heating the catalyst to a temperature that did not exceed 500° C. in a stream of nitrogen. The residence time of the catalyst in the heated zone was two minutes.

The catalyst was then impregnated for two hours at room temperature in an anhydrous ethanolic solution containing 525 ppm of cesium chloride. The solution was drained and an equal volume of ethanol was added. The catalyst was mixed with the fresh ethanol to remove any excess cesium present on its surface. The liquid was drained, and the catalyst was dried by placing it on a belt that travelled through a heated zone of a furnace in a current of 200° C. air. The residence time in the hot zone, the air flow and the furnace temperature were sufficient to dry all the solvent in the shortest time possible.

After drying the catalyst, it was tested in a tube that is heated by a salt bath. A gas mixture containing 15% ethylene, 7% oxygen, and 78% inert, mainly nitrogen and carbon dioxide, was allowed to flow over the catalyst under 300 p.s.i. The temperature of the reaction was adjusted in order to obtain ethylene oxide productivity of 160 Kg per hour per m³ of catalyst. The results of the catalyst test are summarized in table 4:

TABLE 8

| Time in Reactor Hr | Selectivity % | Reaction Temperature °C. |
| --- | --- | --- |
| 140 | 82.2 | 233 |

EXAMPLE 10

The support used for this preparation was obtained from Norton Company and was made primarily of α-alumina in the form of 5/16 inch cylinders. The support has a surface area of 0.55 m²/g, pore volume of 0.3 cc/g, and medium pore diameter of 1.5μ. 95 parts of a cumene solution of silver neodecanoate, containing 26% silver, was added to 225 parts of the hot support and the mixture was mixed for 30 minutes. The deposition of silver was induced by heating the catalyst to a temperature that did not exceed 200° C. in a stream of nitrogen. The residence time of the catalyst in the heated zone was two minutes. This process was repeated at 300° C. and 400° C.

The catalyst was then impregnated for two hours at room temperature in an anhydrous ethanolic solution containing 525 ppm of cesium carbonate. The liquid was drained, and the catalyst was dried by placing it on a belt that travelled through a heated zone of a furnace in a current of 200° C. air. The residence time in the hot zone, the air flow and the furnace temperature were sufficient to dry all the solvent in the shortest time possible.

After drying the catalyst, it was tested in a tube that is heated by a salt bath. A gas mixture containing 15% ethylene, 7% oxygen, and 78% inert, mainly nitrogen and carbon dioxide, was allowed to flow over the catalyst under 300 p.s.i. The temperature of the reaction was adjusted in order to obtain ethylene oxide productivity of 160 Kg per hour per m³ of catalyst. The results of the catalyst test are summarized in table 5:

TABLE 9

| Time in Reactor Hr | Selectivity % | Reaction Temperature °C. |
| --- | --- | --- |
| 100 | 82.5 | 231 |

TABLE 9-continued

| Time in Reactor Hr | Selectivity % | Reaction Temperature °C. |
| --- | --- | --- |
| 300 | 82.7 | 230 |
| 450 | 83.0 | 230 |

EXAMPLE 11

The support used for this preparation was obtained from Norton Company and was made primarily of α-alumina in the form of 5/16 inch cylinders. The support has a surface area of 0.55 m²/g, pore volume of 0.3 cc/g, and medium pore diameter of 1.5μ. 95 parts of a cumene solution of silver neodecanoate, containing 26% silver, was added to 225 parts of the hot support and the mixture was mixed for 30 minutes.

The deposition of silver was induced by heating the catalyst up to the decomposition temperature of the silver salt. This was achieved via heating in a furnace that has several heating zones in a controlled atmosphere. The catalyst was loaded on a moving belt that entered the furnace at ambient temperature, which was gradually increased as the catalyst passed from one zone to the next. The temperature was increase, up to 500° C., as the catalyst passed through seven heating zones. After the heating zones the belt passed through a cooling zone that gradually cooled the catalyst to a temperature lower than 100° C. The total residence time in the furnace was 22 minutes. The atmosphere of the furnace was controlled to eliminate uncontrolled combustion of the organic portion of the silver salt and solvent. This was achieved via using nitrogen flow in the different heating zones. The amount of nitrogen was sufficient to inhibit any combustion and to remove any evolved fumes during the calcination process.

The catalyst was then impregnated for two hours at room temperature in an ethanolic solution of cesium bicarbonate. The catalyst was dried and tested in a tube that is heated by a salt bath. A gas mixture containing 15% ethylene, 7% oxygen and 78% inert, mainly nitrogen and carbon dioxide, was allowed to flow over the catalyst under 300 p.s.i. The temperature of the reaction was adjusted in order to obtain ethylene oxide productivity of 160 Kg per hour per m3 of catalyst. The results of the catalyst test are summarized in Table 10 below:

TABLE 10

| Catalyst life, hr | Temp. °C. | Selectivity, % |
| --- | --- | --- |
| 200 | 229 | 82.55 |

The invention claimed is:
1. A process for the production of ethylene oxide comprising the steps of:
  (a) impregnating a porous support having a surface area of about 0.2 to 2.0 m²/g with a hydrocarbon solution of a silver salt of a neo acid sufficient to provide 3 to 20 wt % silver on the support;
  (b) subjecting the silver impregnated support of step (a) to activation in an atmosphere containing less oxygen than air by heating at a first temperature in the range of 150° to 200° C. for less than an hour, heating at a second temperature in the range of from greater than 200° C. to 300° C. for less than one hour, heating at a third temperature in the range of from greater than 300° C. to 400° C. for less than one hour and finally heating at a fourth temperature of from greater than 400° C. to 500° C.; and (d) passing ethylene and molecular oxygen over the silver impregnated support of step (c) at a temperature of between 150° C. to 400° C. and a pressure of between 0.5 to 35 bar.

2. The process according to claim 1 wherein said first activation is carried out in an atmosphere containing less than 20 vol % oxygen.

3. The process according to claim 2 wherein said activation is carried out on a moving belt.

4. The process according to claim 3 wherein the retention time of the impregnated support at said first temperature is from about 2 to 30 minutes.

5. The process according to claim 3 wherein the retention time of the impregnated support at said second temperature is from about 2 to 30 minutes.

6. The process according to claim 3 wherein the retention time of the impregnated support at said third temperature is from about 2 to 30 minutes.

7. The process according to claim 1 further comprising the step of impregnating the activated silver impregnated support of step (b) with a solution containing an alkali metal to obtain a finished catalyst having about 1 to $6 \times 10^{-3}$ gew of the alkali metal per kg of catalyst.

8. The process according to claim 7 wherein said alkali metal is cesium.

9. The process according to claim 8 wherein said cesium is contained in a substantially anhydrous alcohol solution.

10. The process according to claim 9 wherein said cesium impregnated silver catalyst is washed with an alcohol solution and dried.

11. The process according to claim 10 wherein there are multiple alcohol washes.

12. The process according to claim 2 wherein said atmosphere is substantially nitrogen.

13. The process according to claim 2 wherein said atmosphere is substantially carbon dioxide.

14. The process according to claim 2 wherein said atmosphere is substantially helium.

15. The process according to claim 1 wherein the quantity of said hydrocarbon solution used to impregnate said porous support is no more than necessary to fill the pore volume of said porous support.

* * * * *